US008849386B2

(12) United States Patent
Waters (10) Patent No.: US 8,849,386 B2
(45) Date of Patent: Sep. 30, 2014

(54) ANALYZING ELECTROCARDIOGRAMS (76) Inventor: James Waters, Slingerlands, NY (US)

(*) Notice: Subject to any disclaimer, the term of this patent is extended or adjusted under 35 U.S.C. 154(b) by 0 days.

(21) Appl. No.: 13/539,576

(22) Filed: Jul. 2, 2012

(65) Prior Publication Data
US 2013/0178755 A1 Jul. 11, 2013

Related U.S. Application Data (60) Provisional application No. 61/505,007, filed on Jul. 6, 2011.

(51) Int. Cl.
A61B 5/046 (2006.01)
A61N 1/39 (2006.01)

(52) U.S. Cl.
CPC .............. A61B 5/046 (2013.01); A61N 1/3987 (2013.01); A61N 1/3993 (2013.01)
USPC ................................ 600/518; 607/5; 600/509

(58) Field of Classification Search
None
See application file for complete search history.

(56) References Cited

U.S. PATENT DOCUMENTS 7,171,269 B1    1/2007  Addison et al.
2006/0235320 A1* 10/2006  Tan et al. .................... 600/509

OTHER PUBLICATIONS

Woflfram MathWorld, "Lorentzian Function," Accessed Oct. 8, 2013, Wolfram Research, http://mathworld.wolfram.com/LorentzianFunction.html.*
Watson et al., A novel wavelet transform based analysis reveals hidden structure in ventricular fibrillation, Resuscitation 43, 2000, pp. 121-127.
Paul S. Addison, Topical Review, Wavelet transforms and the ECG: a review, Institute of Physics Publishing, Physiological Measurement 26, 2005, pp. R155-R199.
L. Khadra et al., Detection of life-threatening cardiac arrhythmias using the wavelet transformation, Medical & Biological Engineering & Computing 35, 1997, pp. 626-632.

* cited by examiner

Primary Examiner — Michael Kahelin
(74) Attorney, Agent, or Firm — David E. Rook; Hoffman Warnick LLC (57) ABSTRACT An electrocardiogram (ECG) analyzing system for analyzing electrocardiogram (ECG) signals, the system including: a computing device including: a transformer for transforming an ECG signal into a time-frequency representation over a plurality of frequencies over a period of time; a calculator for calculating a magnitude of the time-frequency representation; an analyzer for analyzing a degree of clustering of a plurality of low-magnitude values in the time-frequency representation; and a diagnosing system for diagnosing whether ventricular fibrillation is present based on the degree of clustering.

20 Claims, 12 Drawing Sheets

ANALYZING ELECTROCARDIOGRAMS

BACKGROUND OF THE INVENTION

Embodiments of this invention relate generally to electrocardiograms (ECGs) and more particularly to analyzing ECGs to diagnose ventricular fibrillation.

ECGs depict electrical activity of the heart over time. Electrical activity is detected by electrodes placed at different locations on the body. The 12 lead ECG is well known to those skilled in the art. Each lead depicts electrical activity along a distinct axis of the heart. Electrical activity in the heart stimulates contraction of the heart muscle, resulting in a cycle of contraction and relaxation. The electrical activity associated with these contractions may be visualized with an ECG, providing information about the activity of the heart muscle.

Figure 1:
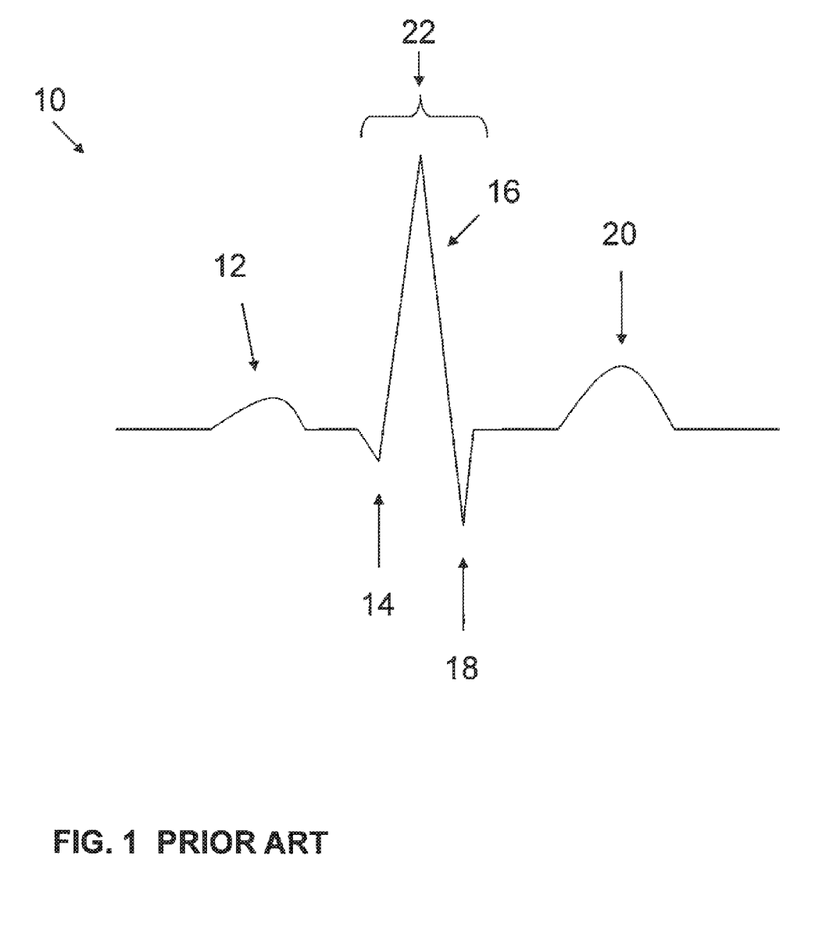
FIG. 1 shows a schematic representation of one known contraction of a heart within normal limits.

Referring to FIG. 1, a schematic representation of one known contraction of a heart within normal limits is shown. A contraction 10 of the heart with a normal sinus rhythm may result in generating a P wave 12, a Q wave 14, an R wave 16, an S wave 18, and a T wave 20. With respect to a cardiac rhythm, a QRS complex 22 represents a rapid contraction of the ventricles of the heart. A person skilled in the art will readily recognize these features and others of the normal sinus rhythm. A person skilled in the art will readily recognize that the heart within normal limits may exhibit many variations on the representation shown in FIG. 1 and that a skilled diagnostician may be needed to distinguish these variations and what those variations represent.

Figure 2:
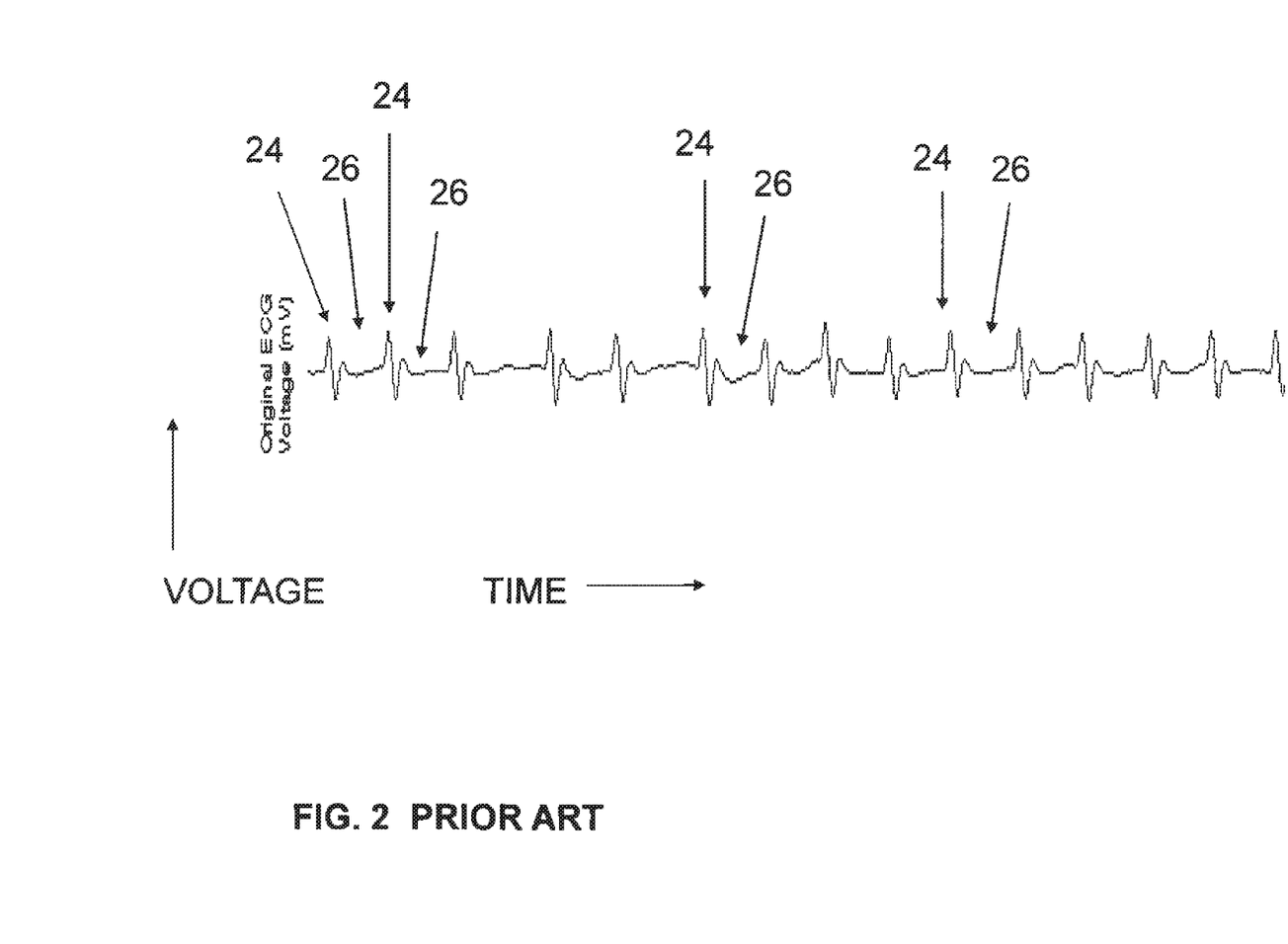
FIGS. 2 and 3 show schematic representations of a known rhythm strip of an ECG of the heart within normal limits.
Figure 3:
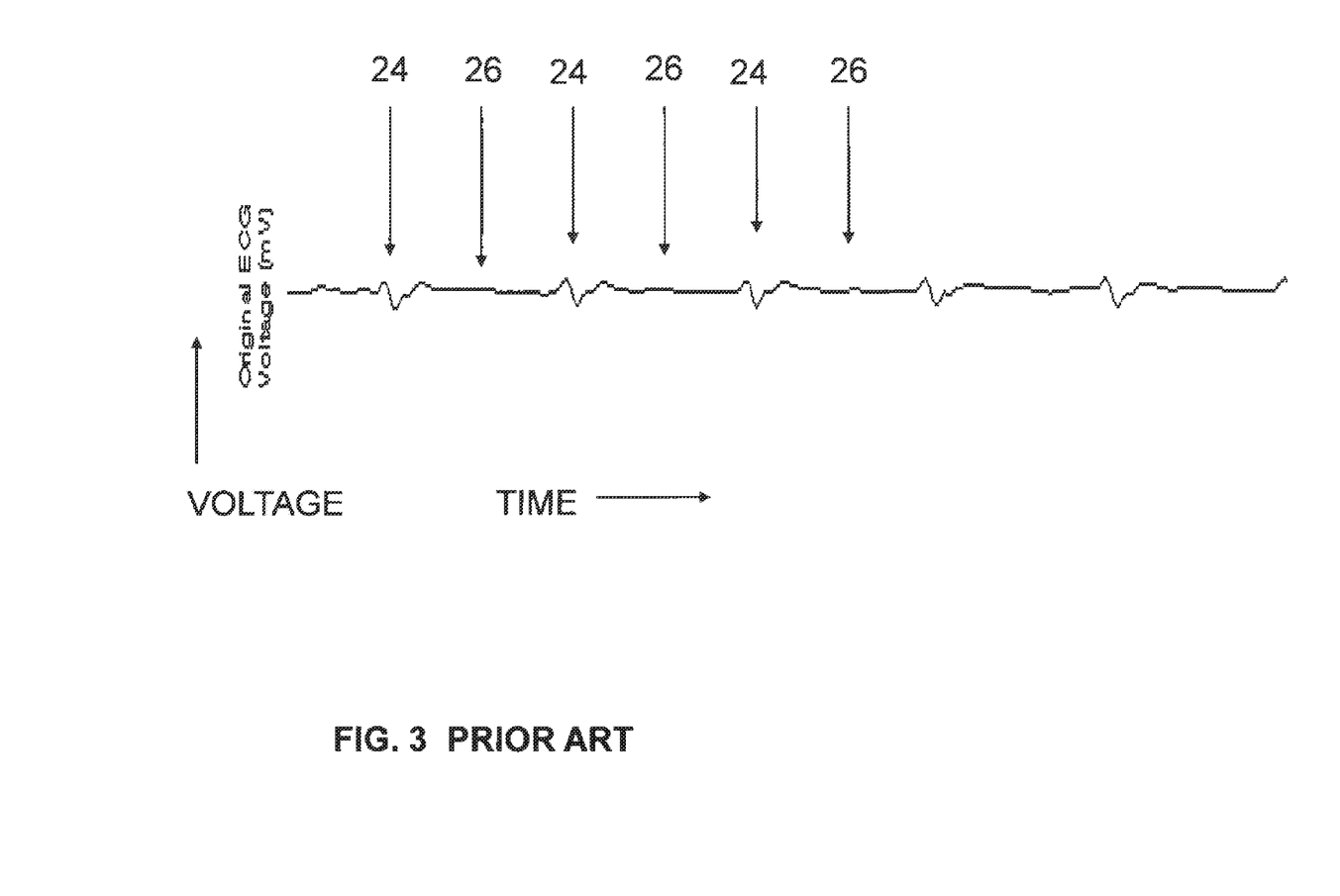

Referring to FIG. 2, a schematic representation of a known rhythm strip of an ECG of the heart within normal limits is shown. The known rhythm strip shows electrical activity of the heart over time. A series of ventricular contractions 24 and relaxations 26 may be seen on the known rhythm strip. Referring to FIG. 3, a schematic representation of a known rhythm strip of the heart within normal limits is shown. A series of ventricular contractions 24 and relaxations 26 may be seen on the known rhythm strip. In comparison to FIG. 2, the contractions shown in FIG. 3 are less distinct but the relaxation 26 between the contractions 24 may be distinguished from the contractions 24. A person skilled in the art will readily recognize that the heart within normal limits may exhibit many variations on the representations shown in FIGS. 2 and 3 and that a skilled diagnostician may be needed to distinguish these variations and what those variations represent. Diagnosing a ventricular rhythm of the heart may be useful for deciding whether to provide emergency intervention to a person. Ventricular fibrillation (VF) is a leading cause of death in the developed world. The standard of care for VF is to initiate cardiopulmonary resuscitation (CPR) and, when available, attach an external defibrillator to deliver an electrical shock. An automated external defibrillator (AED) may be used to administer an electrical shock to the person. Prior to allowing the administration of the electrical shock, the AED may require that VF be detected. Current AEDs may require cessation of CPR and a delay of up to twenty seconds in order to diagnose a ventricular rhythm. In the person requiring defibrillation, the delay of up to twenty seconds may decrease the chance of resuming spontaneous circulation and lower the probability of neurologically intact survival.

Figure 4:
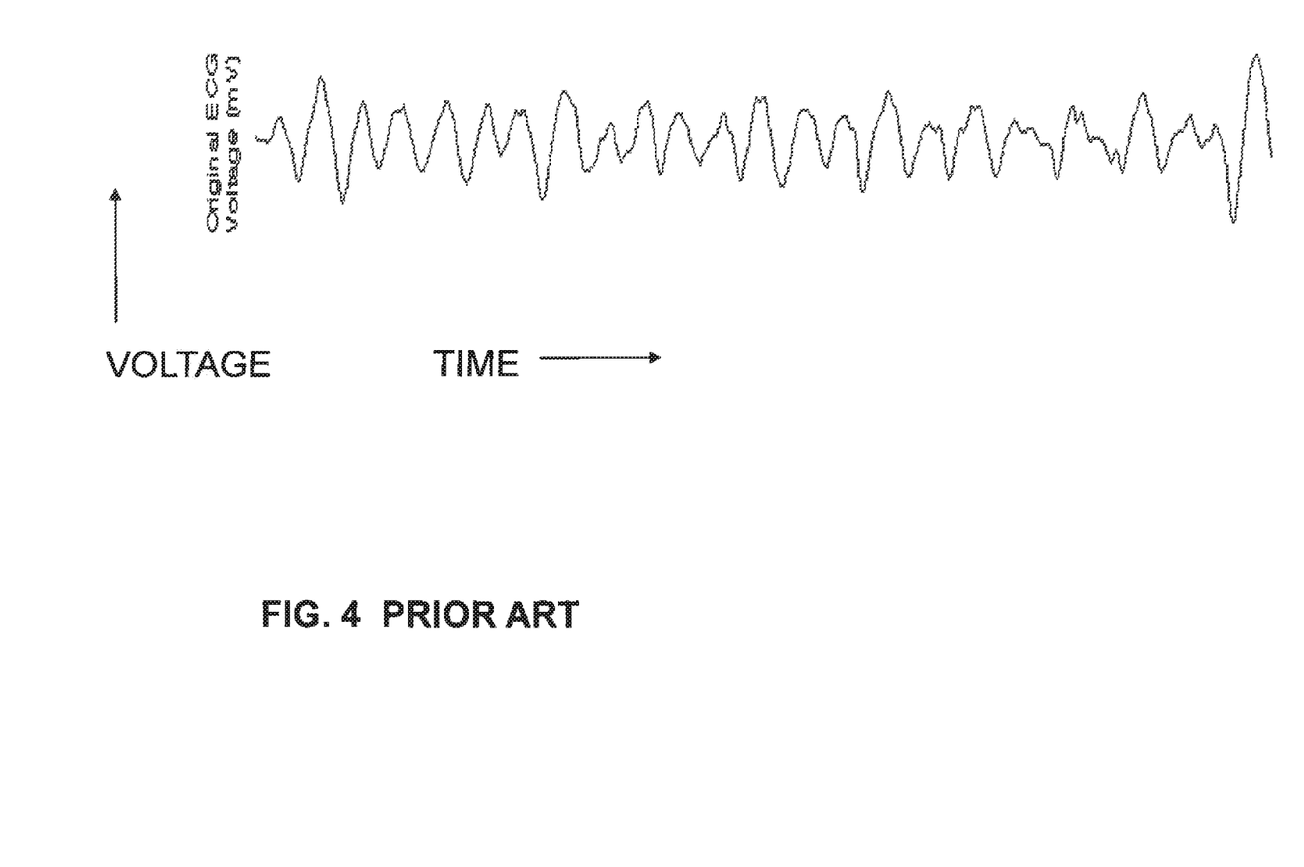
FIG. 4 shows a schematic representation of a known rhythm strip of an ECG of the heart with ventricular fibrillation.

Referring to FIG. 4, a schematic representation of a known rhythm strip of an ECG of the heart with ventricular fibrillation is shown. In VF the ventricles contract in an uncoordinated fashion. The ventricles exhibit essentially continuous activity with different parts of the heart muscle depolarizing at different times, and the ECG does not show distinct ventricular contractions 24, FIGS. 2, 3 or recognizable ventricular relaxations 26, FIGS. 2, 3 (quiescent periods). Under the circumstance represented by FIG. 4, the heart's ventricles may be contracting relatively continuously and the individual may be diagnosed as suffering from ventricular fibrillation (VF).

SUMMARY OF THE INVENTION

A first aspect of the invention includes a system for analyzing electrocardiogram (ECG) signals, the system comprising: a computing device including: a transformer for transforming an ECG signal into a time-frequency representation over a plurality of frequencies over a period of time; a calculator for calculating a magnitude of the time-frequency representation; an analyzer for analyzing a degree of clustering of a plurality of low-magnitude values in the time-frequency representation; and a diagnosing system for diagnosing whether ventricular fibrillation is present based on the degree of clustering.

A second aspect of the invention includes a method for analyzing electrocardiogram (ECG) signals, the method comprising: transforming an ECG signal into a time-frequency representation over a plurality of frequencies over a period of time; calculating a magnitude of the time-frequency representation; analyzing a degree of clustering of a plurality of low-magnitude values in the time-frequency representation; diagnosing whether ventricular fibrillation is present based on the degree of clustering.

A third aspect of the invention includes a computer program product comprising program code embodied in at least one computer-readable storage medium, which when executed, enables a computing device to implement a method, the method comprising: transforming an ECG signal into a time-frequency representation over a plurality of frequencies over a period of time; calculating a magnitude of the time-frequency representation; analyzing a degree of clustering of a plurality of low-magnitude values in the time-frequency representation; diagnosing whether ventricular fibrillation is present based on the degree of clustering.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION

Figure 5:
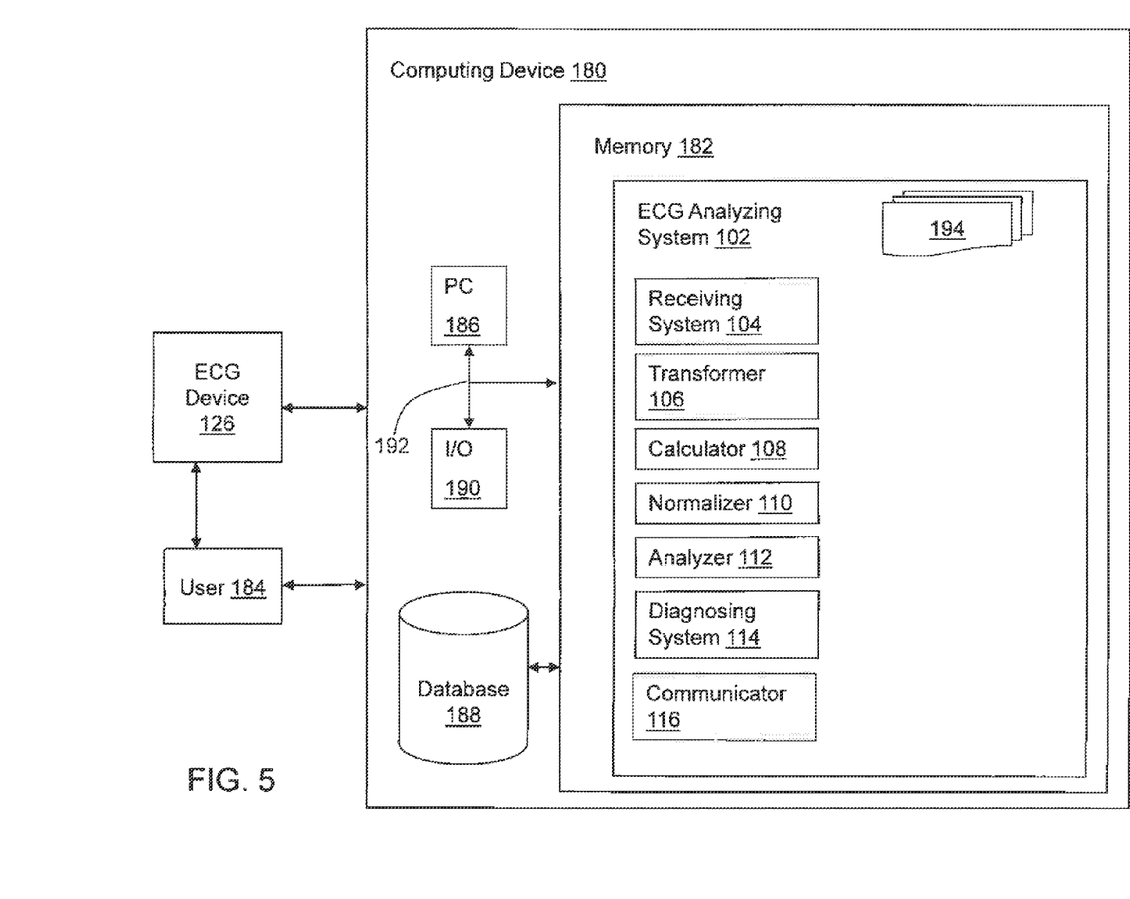
FIG. 5 shows a block diagram of one embodiment of an ECG analyzing system in accordance with the invention.

Referring to FIG. 5, a block diagram of one embodiment of an electrocardiogram (ECG) analyzing system 102 in accordance with the invention is shown. ECG analyzing system 102 may include a receiving system 104, a transformer 106, a calculator 108, a normalizer 110, an analyzer 112, a diagnosing system 114, and a communicator 116. A computing device 180 may include memory 182, which makes computing device 180 operable to perform steps described herein. As indicated in FIG. 5, the receiving system 104, the transformer 106, the calculator 108, the normalizer 110, the analyzer 112, the diagnosing system 114, and the communicator 116 may be optional components (or, modules) in ECG analyzing system 102. Alternatively, the receiving system 104, the transformer 106, the calculator 108, the normalizer 110, the analyzer 112, the diagnosing system 114, and the communicator 122 may be part of an external system which may perform the functions described herein. Computing device 180 is shown in communication with ECG device 126 and/or a user 184. ECG device 126 is shown in communication with the user 184. User 184 may be a human, for example, a programmer or operator and/or a computerized system interacting with computing device 180 and/or ECG device 126.

Figure 6:
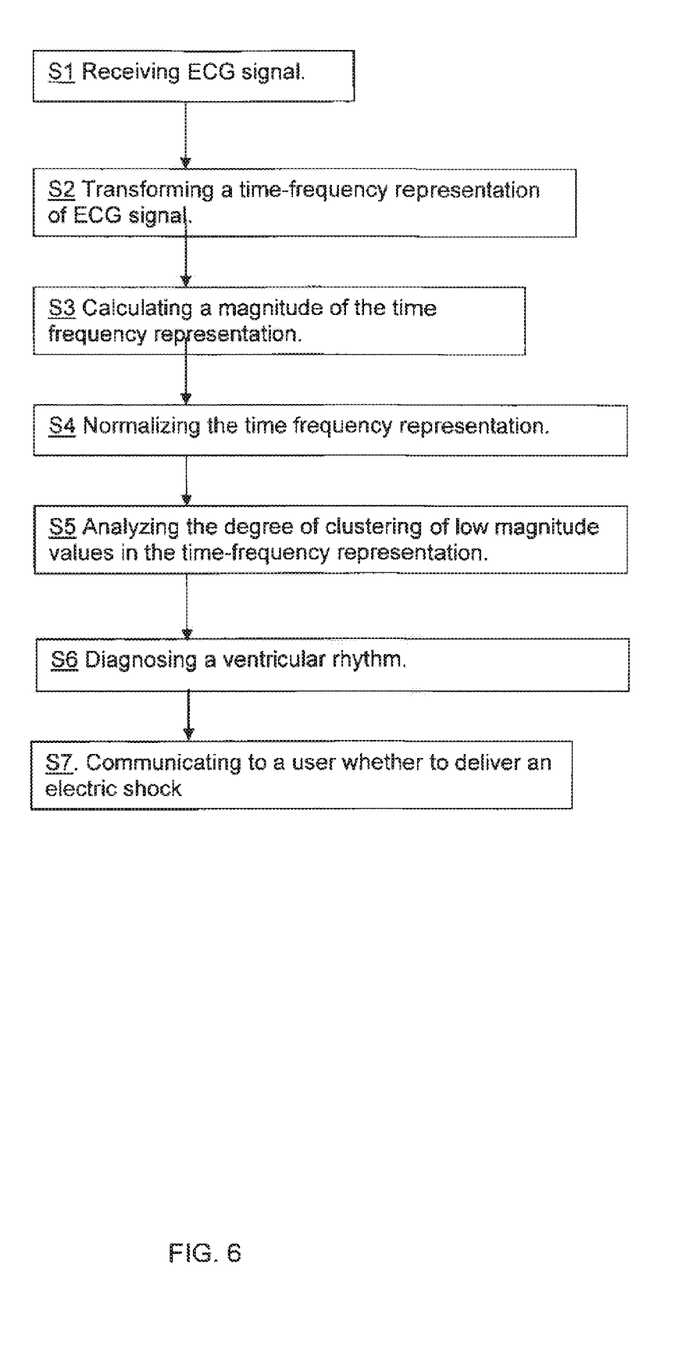
FIG. 6 shows a flow diagram for use in describing a method according to an embodiment of the invention.

Referring to FIG. 6, a flow diagram of a method of analyzing ECGs in one embodiment of the invention is shown. As shown in FIG. 6, at S1, receiving system 104 may receive an ECG signal from ECG device 126. ECG signal may be provided by any ECG device 126. ECG device 126 may include, for example, a defibrillator and an AED. At S2, transformer 106 may transform the ECG signal into a time-frequency representation over a plurality of frequencies over a period of time providing an estimate of a contribution of each of a plurality of frequencies to the overall signal at each point in time. Time-frequency transforms that may be used include a short-time Fourier transform, a wavelet transform, an approximation of a wavelet transform using a discrete Fourier transform, and a chirplet transform.

For example, the time-frequency representation of the ECG signal may be calculated using the wavelet transform:

$$T(a, b) = \frac{1}{w(a)} \int_{-\infty}^{\infty} \bar{\psi}\left(\frac{t-b}{a}\right) x(t) dt$$

where x(t) is the ECG signal magnitude at time t, $$\psi\left(\frac{t-b}{a}\right)$$

is the mother wavelet at scale a and time a, $\bar{\psi}(t)$ is the complex conjugate of the wavelet function $\psi(t)$, and w(a) is a scaling function usually of the form w(a)=α or w(a)=$\sqrt{a}$.

Various wavelets may be employed. An example is the complex Morlet wavelet:

$$\psi(t) = \frac{1}{\sqrt[4]{\pi}} e^{i\omega_0 t} e^{\frac{t^2}{2}}$$

Where $\omega_0$ is the center frequency of the mother wavelet. If a complex wavelet is used, the values in the time-frequency representation may also contain complex values.

At S3, calculator 106 may calculate a magnitude of the time-frequency representation. The magnitude of the time-frequency representation may be calculated as:

$$M(a,b)=|T(a,b)|^k$$

where k is usually 1 or 2. The result M(a,b) may consist of real values even if the original time-frequency representation included complex values.

Figure 7A:
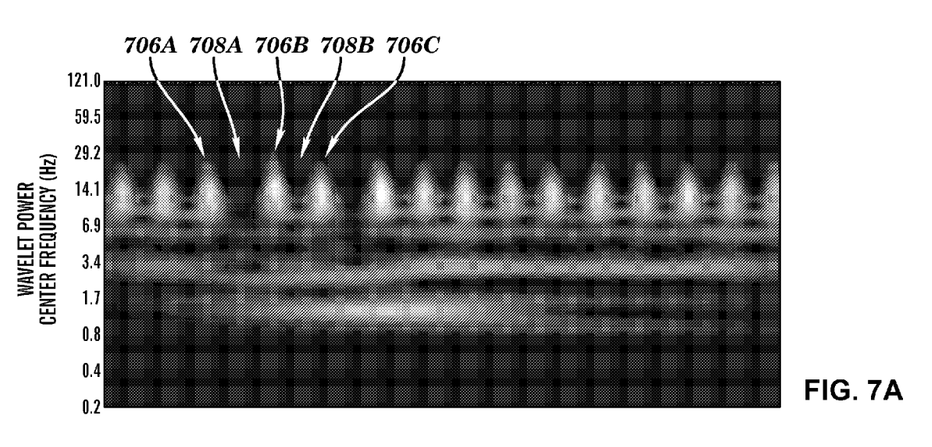
FIGS. 7A, 9A, and 11A show a graphical view of one embodiment of a display of ECG data in accordance with the invention.
Figure 9A:
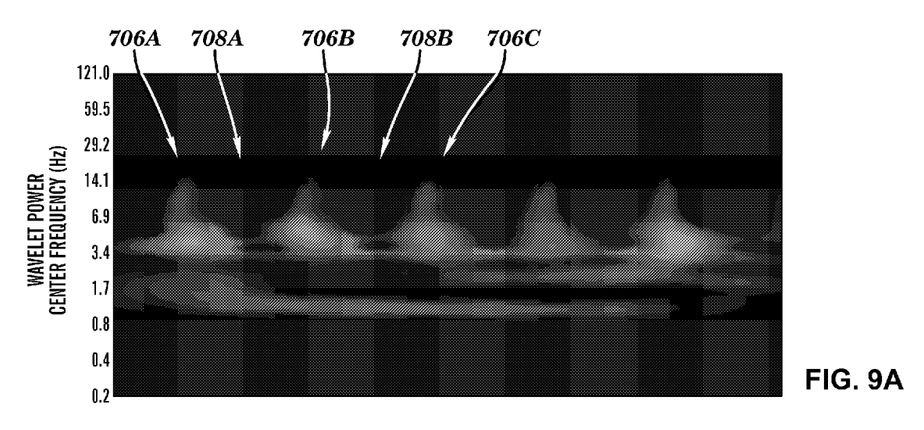
Figure 11A:
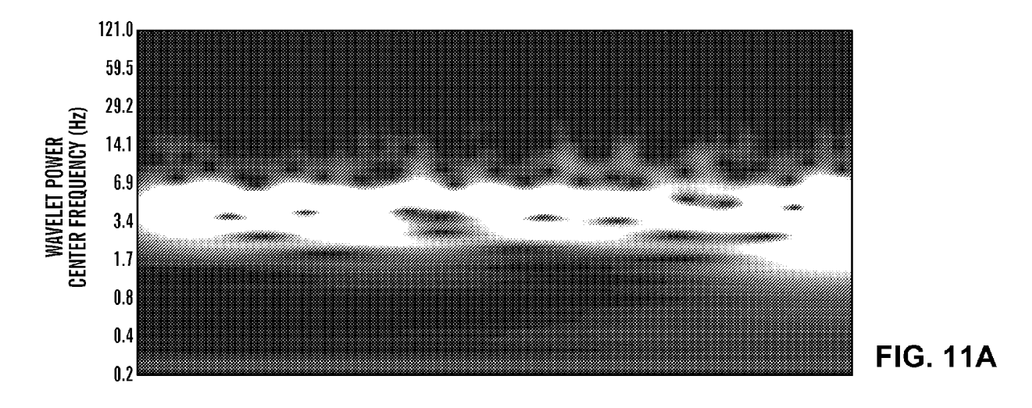

Referring to FIGS. 7A, 9A, and 11A, schematic representations of the magnitudes of time-frequency representations associated with ECG rhythm strips shown in FIGS. 2, 3, and 4 respectively are shown. Light shades 702 on the schematic represent high magnitudes; dark shades 704 represent low magnitudes. FIGS. 7A and 9A show the magnitudes of the time-frequency representation of the ECG signal of a heart with an organized rhythm. FIG. 11A shows the magnitudes of a time-frequency representation of the ECG signal of a heart in ventricular fibrillation. In FIGS. 7A and 9A, a series of peaks 706A, 706B, 706C are shown with spaces 708A, 708B between every two successive peaks 706A-706B and 706B, 706C each peak 706A, 706B, 706C representing the QRS complex of the contraction of the heart and each space 708A, 708B representing the relaxation of the heart. FIGS. 7A and 9A, show the peaks 706A, 706B, 706C and the spaces 708A, 708B to be distinguishable in the 2-25 Hz range. In FIG. 11A, there is substantially no distinction of the series of peaks 706A, 706B, 706C FIGS. 7A, 9A and substantially no spaces 708A, 708B FIGS. 7A, 9A discernable in the 2-25 Hz range. The number of low-magnitude data points is less than in FIGS. 7A and 9A and the clusters of low-magnitude data points are smaller in area. FIG. 11A represents ventricular fibrillation.

FIGS. 7A, 9A, and 11A illustrate optional steps of the invention but are not required to perform the other steps described herein.

At S4, normalizer 110 may normalize the time-frequency representation such that a total magnitude at each frequency is equalized:

$$M'(a, b) = \frac{M(a, b)}{\sum_{-\infty}^{\infty} M(a, i)}$$

The normalization may extend the frequency at which VF may be distinguished from organized rhythm up to approximately 30 Hz. As a result, the time-frequency representation may be examined at frequencies between approximately 12 and 28 Hz. Examining in the approximately 12-28 Hz range may allow the detection of VF while ignoring higher and lower frequencies at which the distinction between organized rhythm and VF may be less consistent.

Figure 7B:
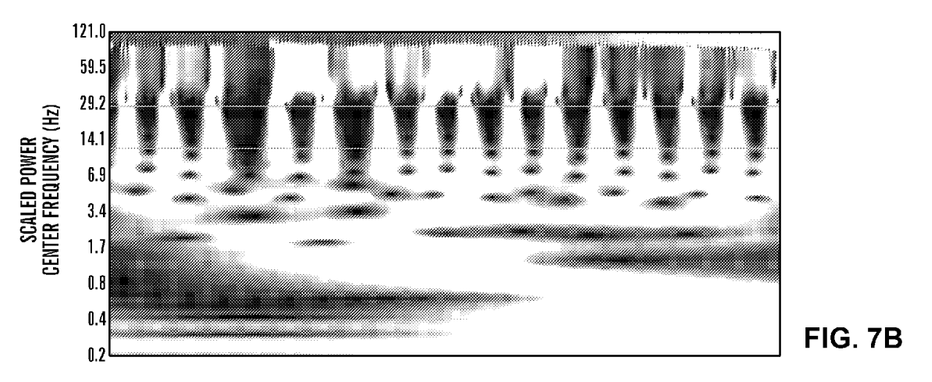
FIGS. 7B, 9B, and 11B show a graphical view of one embodiment of a display of ECG data in accordance with the invention.
Figure 9B:
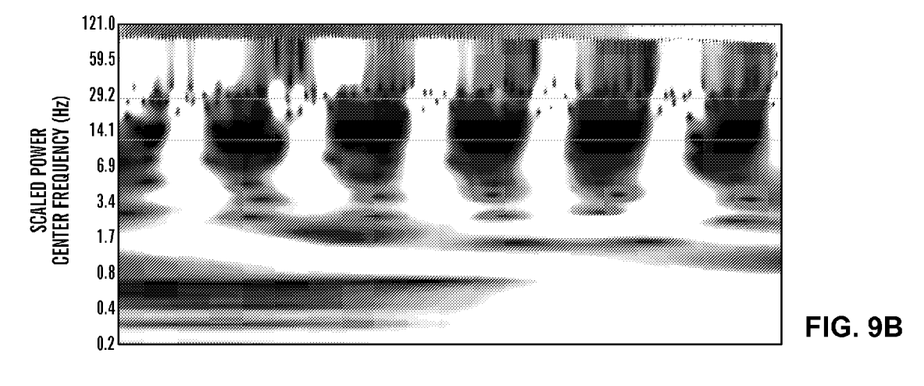
Figure 11B:
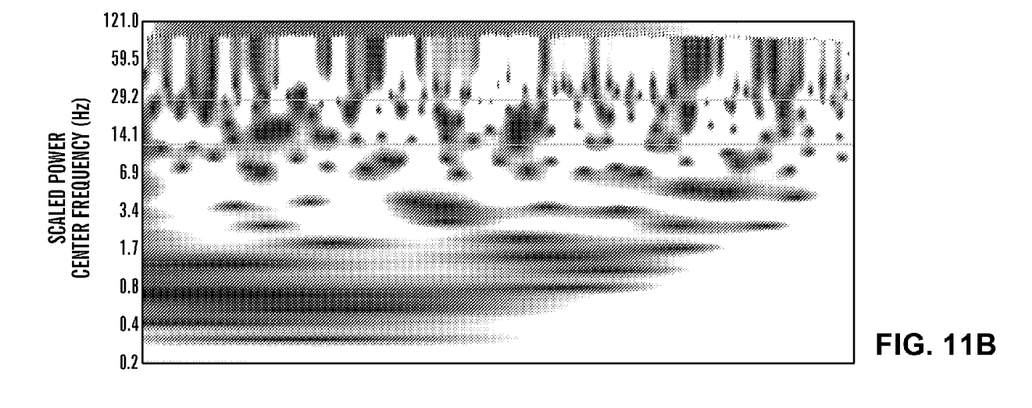

Referring to FIGS. 7B, 9B, and 11B, schematic representations of normalized time-frequency representations associated with the ECG rhythm strips in FIGS. 2, 3, and 4 and the magnitudes of time-frequency representations in FIGS. 7A, 9A, and 11A respectively are shown. FIGS. 7B and 9B show normalized time-frequency representations associated with an ECG rhythm strip of a heart with organized rhythm. FIG. 11B shows a normalized time-frequency representation associated with an ECG rhythm strip of a heart in ventricular fibrillation.

FIGS. 7B, 9B, and 11B illustrate optional steps of the invention but are not required to perform the other steps described herein.

At S6, analyzer 112 may analyze a degree of clustering of low-magnitude values in the time-frequency representation.

Figure 8:
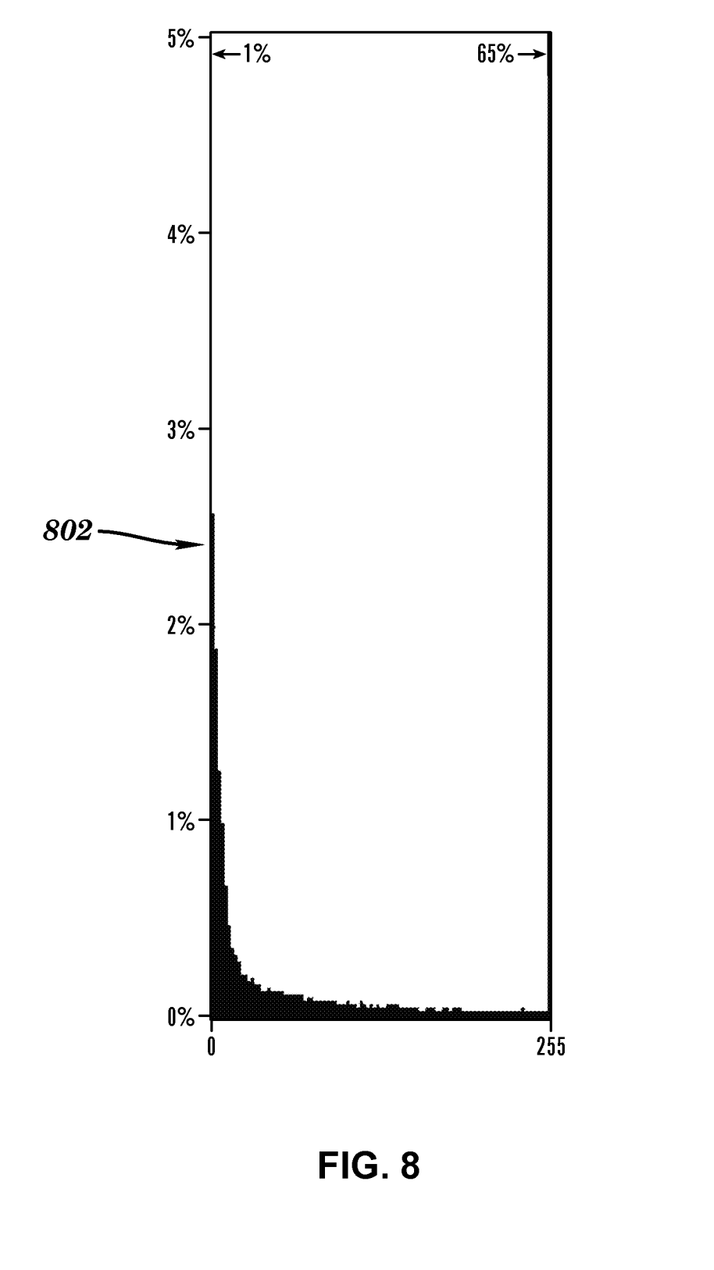
FIGS. 8, 10, and 12 show a graphical view of one embodiment of a display of ECG data in accordance with the invention.
Figure 10:
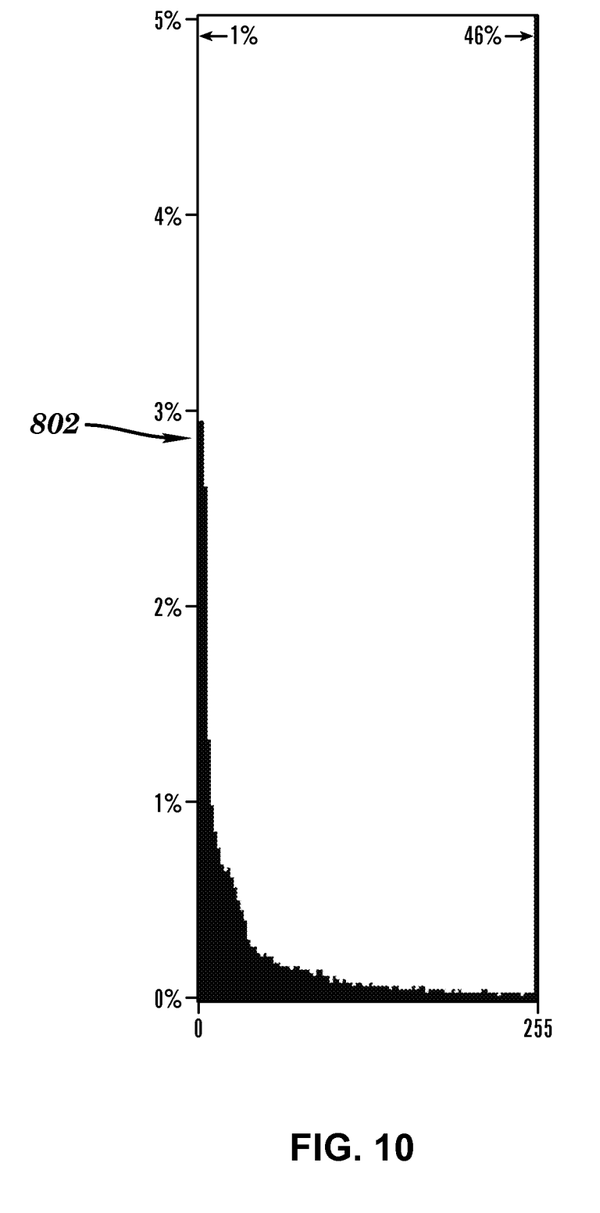
Figure 12:
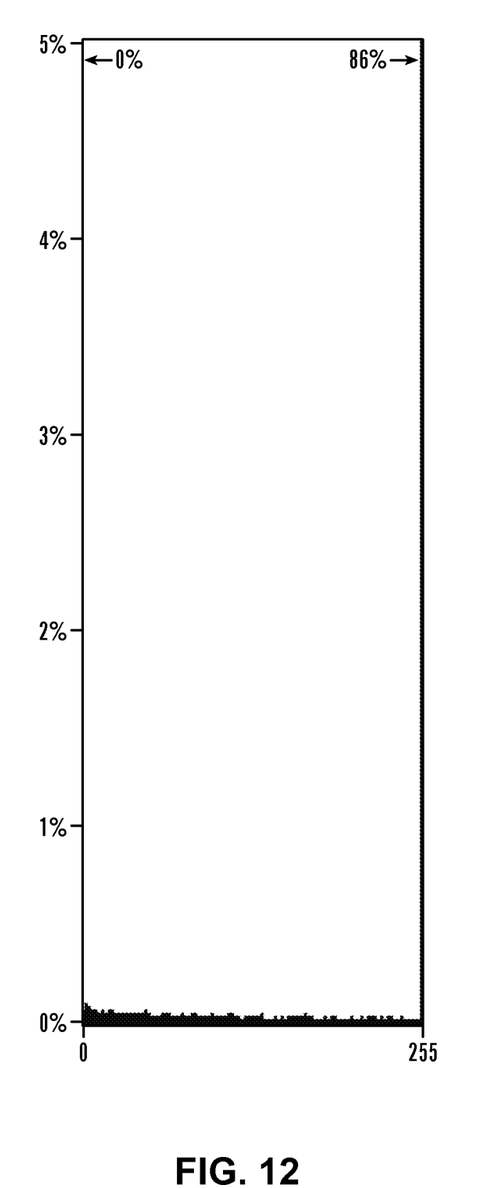

The analyzer may construct a histogram representing the magnitude at each frequency and each time point in the time-frequency representation. Referring to FIGS. 8, 10, and 12, schematic representations of constructed histograms associated with the ECG rhythm strips in FIGS. 2, 3, and 4, the calculated magnitudes of the time-frequency spectra in FIGS. 7A, 9A, and 11A, and the normalized time-frequency representation in FIGS. 7B, 9B, and 11B, respectively, are shown. FIGS. 8 and 10 show constructed histograms associated with ECG signals of hearts with organized rhythm. FIGS. 8 and 10 show a distinct peak 802 as the magnitude approaches zero. FIG. 12 shows a constructed histogram associated with an ECG rhythm strip of a heart in ventricular fibrillation. FIG. 12 does not show a distinct peak 802 as the magnitude approaches zero. The degree of clustering may be analyzed by summing the contents of the n lowest-magnitude histogram bins where n is a predetermined bin count. Additionally or alternatively, the degree of clustering may be analyzed by calculating the statistical entropy of the p lowest-magnitude bins where p is a predetermined bin count. Additionally or alternatively, the degree of clustering may be analyzed by calculating the extent to which low-magnitude values are clustered along the time and frequency axes using methods that may include cluster analysis, mathematical morphology analysis and watershed analysis.

FIGS. 8, 10, and 12 illustrate optional steps of the invention but are not required to perform the other steps described herein.

At S6, diagnosing system 114 may diagnose VF by comparing the degree of clustering to a predefined threshold. At S7, communicator 116 may communicate to the user whether to deliver an electric shock. Alternatively, communicator 116 may communicate to the user that a shock is about to be delivered and then initiate a shock without further user input. Electric shock may be administered by the ECG device 126 or a separate component may deliver the electric shock.

A person skilled in the art will readily recognize that user 184 who is a first responder, medical technician, nurse, doctor or any other trained individual may make decisions concerning starting, resuming, and ceasing cardiopulmonary resuscitation and may make decisions concerning whether or not to administer the electric shock. Any number of factors evaluated at the time of responding to person's health needs may affect the decision or decisions user makes.

Referring again to FIG. 5, communications between user 184 and computing device 180 can be implemented using any solution, such as an audio interface, a graphical interface, an application programming interface (API), and/or the like. Furthermore, communications can utilize any combination of public and/or private networks. Computing device 180 is shown including a processing component 186 (e.g., one or more processors), a database 188, memory 182, an input/output (I/O) component 190 (e.g., one or more I/O interfaces and/or devices), and a communications pathway 192. In one embodiment, processing component 186 executes program code, such as ECG analyzing system 102, which is at least partially embodied in memory 182. While executing program code, processing component 186 can process data, which can result in reading and/or writing the data to/from database 188, memory 182 and/or I/O component 190 for further processing. Communications pathway 192 provides a communications link between each of the components in computing device 180. I/O component 190 can comprise one or more human I/O devices or storage devices, which enable user 184 to interact with computing device 180 and/or one or more communications devices to enable user 184 to communicate with computing device 180 using any type of communications link. To this extent, electrocardiogram (ECG) analyzing system 102 can manage a set of interfaces (e.g., audio interface, graphical user interface(s), application program interface, and/or the like) that enable human and/or system interaction with electrocardiogram (ECG) analyzing system 102.

In any event, computing device 180 can comprise one or more general purpose computing articles of manufacture (e.g., computing devices) capable of executing program code installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, electrocardiogram (ECG) analyzing system 102 can be embodied as any combination of system software and/or application software. In any event, the technical effect of computing device 180 is to transform, calculate, analyze, diagnose, normalize, and communicate as more fully described herein.

Further, electrocardiogram (ECG) analyzing system 102 can be implemented using a set of modules 194. In this case, a module 194 can enable computing device 180 to perform a set of tasks used by electrocardiogram (ECG) analyzing system 102, and can be separately developed and/or implemented apart from other portions of electrocardiogram (ECG) analyzing system 102. Electrocardiogram (ECG) analyzing system 102 may include modules 194 which comprise a specific use machine/hardware and/or software. Regardless, it is understood that two or more modules, and/or systems may share some/all of their respective hardware and/or software. Further, it is understood that some of the functionality discussed herein may not be implemented or additional functionality may be included as part of computing device 180.

When computing device 180 comprises multiple computing devices, each computing device may have only a portion of ECG analyzing system 102 embodied thereon (e.g., one or more modules 194). However, it is understood that computing device 180 and electrocardiogram (ECG) analyzing system 102 are only representative of various possible equivalent computing devices that may perform a process described herein. To this extent, in other embodiments, the functionality provided by computing device 180 and electrocardiogram (ECG) analyzing system 102 can be at least partially implemented by one or more computing devices that include any combination of general and/or specific purpose hardware with or without program code. In each embodiment, the hardware and program code, if included, can be created using standard engineering and programming techniques, respectively.

Regardless, when computing device 180 includes multiple computing devices, the computing devices can communicate over any type of communications link. Further, while performing a process described herein, computing device 180 can communicate with one or more other computing devices using any type of communications link. In either case, the communications link can comprise any combination of various types of wired and/or wireless links; comprise any combination of one or more types of networks; and/or utilize any combination of various types of transmission techniques and protocols.

As discussed herein, electrocardiogram (ECG) analyzing system 102 enables computing device 180 to transform, calculate, analyze, diagnose, normalize, and communicate as more fully described herein. Electrocardiogram (ECG) analyzing system 102 may include logic, which may include the following functions: receiving system 104, transformer 106, a calculator 108, a normalizer 110, an analyzer 112, a diagnosing system 114, and a communicator 116. In one embodiment, electrocardiogram (ECG) analyzing system 102 may include logic to perform the below-stated functions. Structurally, the logic may take any of a variety of forms such as a field programmable gate array (FPGA), a microprocessor, a digital signal processor, an application specific integrated circuit (ASIC) or any other specific use machine structure capable of carrying out the functions described herein. Logic may take any of a variety of forms, such as software and/or hardware. However, for illustrative purposes, electrocardiogram (ECG) analyzing system 102 and logic included therein will be described herein as a specific use machine. As will be understood from the description, while logic is illustrated as including each of the above-stated functions, not all of the functions are necessary according to the teachings of the invention as recited in the appended claims.

In one embodiment, the invention provides a computer program product embodied in at least one computer-readable storage medium, which when executed, enables a computing device (e.g., computing device 180) to transform, calculate, analyze, diagnose, normalize, and communicate as more fully described herein. To this extent, the computer-readable storage medium includes program code, such as electrocardiogram (ECG) analyzing system 102, which implements some or all of a process described herein. It is understood that the term "computer-readable storage medium" comprises one or more of any type of tangible medium of expression capable of embodying a copy of the program code (e.g., a physical embodiment). For example, the computer-readable storage medium can comprise: one or more portable storage articles of manufacture; one or more memory/storage components of a computing device; paper; and/or the like. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

In another embodiment, the invention provides a method of providing a copy of program code, such as electrocardiogram (ECG) analyzing system 102, which implements some or all of a process described herein. In this case, a computing device can generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computing device receiving the set of data signals described herein, and translating the set of data signals into a copy of the computer program embodied in at least one computer-readable medium. In either case, the set of data signals can be transmitted/received using any type of communications link.

In still another embodiment, the invention provides a method of generating a system for transforming, calculating, analyzing, diagnosing, normalizing, and communicating as more fully described herein. In this case, a computing device, such as computing device 180, can be obtained (e.g., created, maintained, made available, etc.) and one or more modules for performing a process described herein can be obtained (e.g., created, purchased, used, modified, etc.) and deployed to the computing device. To this extent, the deployment can comprise one or more of: (1) installing program code on a computing device from a computer-readable medium; (2) adding one or more computing and/or I/O devices to the computing device; and (3) incorporating and/or modifying the computing device to enable it to perform a process described herein.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An electrocardiogram (ECG) analyzing system comprising:
    a computing device including:
    a transformer for transforming an ECG signal into a time-frequency representation over a plurality of frequencies over a period of time;
    a calculator for calculating a magnitude of the time-frequency representation;
    a normalizer for normalizing the magnitude of the time-frequency representation such that a series of peaks of the time-frequency representation are eliminated and a total magnitude at each frequency is equal before an analyzing;
    an analyzer for the analyzing of a degree of clustering of a plurality of low-magnitude values in the time-frequency representation, wherein the degree of clustering is a characteristic of an area between the eliminated series of peaks; and
    a diagnosing system for diagnosing whether ventricular fibrillation is present based on the degree of clustering of the plurality of low-magnitude values in the time-frequency representation.

2. The system of claim 1, wherein the transforming includes at least one of a short-time Fourier transform, a wavelet transform, an approximation of a wavelet transform using a discrete Fourier transform, and a chirplet transform.

3. The system of claim 1, wherein the analyzing includes a statistical entropy analysis.

4. The system of claim 3, wherein the statistical entropy analysis is calculated with a plurality of p lowest-magnitude bins where p is a predetermined bin count.

5. The system of claim 1, wherein the analyzing includes a cluster analysis.

6. The system of claim 1, wherein the analyzing includes a mathematical morphology analysis.

7. The system of claim 1, wherein the analyzing includes a watershed analysis.

8. The system of claim 1, wherein the analyzing includes summing the contents of a plurality of n lowest-magnitude bins where n is a predetermined bin count.

9. The system of claim 1, further comprising:
a communicator for communicating to a user to administer an electric shock if ventricular fibrillation is present.

10. The system of claim 9, wherein an electric shock is administered by an automated external defibrillator.

11. A method for analyzing an electrocardiogram (ECG), the method comprising:
transforming an ECG signal into a time-frequency representation over a plurality of frequencies over a period of time;
calculating a magnitude of the time-frequency representation;
normalizing the magnitude of the time-frequency representation such that a series of peaks of the time-frequency representation are eliminated and a total magnitude at each frequency is equal before an analyzing;
analyzing of a degree of clustering of a plurality of low-magnitude values in the time-frequency representation, wherein the degree of clustering is a characteristic of an area between the eliminated series of peaks;
diagnosing whether ventricular fibrillation is present based on the degree of clustering of the plurality of low-magnitude values in the time-frequency representation.

12. The method of claim 11, wherein the method of transforming the signal includes at least one of a short-time Fourier transform, a wavelet transform, an approximation of a wavelet transform using a discrete Fourier transform, and a chirplet transform.

13. The non-transitory computer program product of claim 12, wherein the electric shock is administered by an automated external defibrillator.

14. The method of claim 11, wherein the method of analyzing includes a statistical entropy analysis.

15. The method of claim 11, further comprising communicating to a user to administer an electric shock if ventricular fibrillation is present.

16. The method of claim 15, wherein an electric shock is administered by an automated external defibrillator.

17. A non-transitory computer program product comprising program code embodied in at least one computer-readable storage medium, which when executed, enables a computing device to implement a method, the method comprising:
transforming an ECG signal into a time-frequency representation over a plurality of frequencies over a period of time;
calculating a magnitude of the time-frequency representation;
normalizing the magnitude of the time-frequency representation such that a series of peaks of the time-frequency representation are eliminated and a total magnitude at each frequency is equal before an analyzing;
analyzing of a degree of clustering of a plurality of low-magnitude values in the time-frequency representation, wherein the degree of clustering is a characteristic of an area between the eliminated series of peaks;
diagnosing whether ventricular fibrillation is present based on the degree of clustering of the plurality of low-magnitude values in the time-frequency representation.

18. The non-transitory computer program product of claim 17, wherein the method of transforming the signal includes at least one of a short-time Fourier transform, a wavelet transform, an approximation of a wavelet transform using a discrete Fourier transform, and a chirplet transform.

19. The non-transitory computer program product of claim 17, wherein the method of analyzing includes a statistical entropy analysis.

20. The non-transitory computer program product of claim 17, further comprising communicating to a user to administer an electric shock if ventricular fibrillation is present.

* * * * *